United States Patent
Long

(10) Patent No.: US 7,557,719 B1
(45) Date of Patent: Jul. 7, 2009

(54) PATIENT MONITOR PRESSURE PAD WITH EFFECTIVE DATE WARNING ALARM

(75) Inventor: Timothy Long, Novato, CA (US)

(73) Assignee: Smart Caregiver Corporation, Petaluma, CA (US)

(*) Notice: Subject to any disclaimer, the term of this patent is extended or adjusted under 35 U.S.C. 154(b) by 148 days.

(21) Appl. No.: 11/480,784

(22) Filed: Jul. 3, 2006

Related U.S. Application Data

(60) Provisional application No. 60/696,001, filed on Jul. 1, 2005.

(51) Int. Cl.
*G08B 23/00* (2006.01)
*G08B 1/00* (2006.01)
*G08B 21/00* (2006.01)

(52) U.S. Cl. .................. 340/573.4; 340/309.7; 340/666

(58) Field of Classification Search ............... 340/573, 340/573.1, 309.16, 309.2–309.9, 636.1–636.19, 340/573.4, 635, 539.12, 665–668, 568, 548; 73/763; 177/45, 48; 200/85 R See application file for complete search history.

(56) References Cited

U.S. PATENT DOCUMENTS

| | | | | |
|---|---|---|---|---|
| 5,019,803 A * | 5/1991 | Maram | .................... | 340/539.3 |
| 5,361,397 A * | 11/1994 | Wright | ...................... | 340/7.36 |
| 5,410,297 A | 4/1995 | Joseph et al. | | |
| 5,654,694 A | 8/1997 | Newham | | |
| 5,751,214 A | 5/1998 | Cowley et al. | | |
| 6,307,476 B1 * | 10/2001 | Smith et al. | .............. | 340/573.1 |
| 6,950,031 B2 * | 9/2005 | Selig et al. | .................. | 340/666 |
| 6,965,311 B1 * | 11/2005 | Karner | ................... | 340/539.12 |
| 6,985,408 B2 * | 1/2006 | Quine | .......................... | 368/10 |
| 7,283,898 B2 * | 10/2007 | Kamiya | ........................ | 701/34 |
| 7,295,129 B2 * | 11/2007 | Eisenson | ................ | 340/636.1 |
| 2005/0110617 A1 * | 5/2005 | Kile et al. | .............. | 340/286.07 |

* cited by examiner

*Primary Examiner*—Jennifer Mehmood
(74) *Attorney, Agent, or Firm*—Craig M. Stainbrook; Stainbrook & Stainbrook, LLP

(57) ABSTRACT

A patient monitor pressure pad having a time sensor and alarm circuit that produces an audible or visible alarm output to alert facility care staff that the effective life of the pressure pad is nearing its end.

9 Claims, 5 Drawing Sheets

PATIENT MONITOR PRESSURE PAD WITH EFFECTIVE DATE WARNING ALARM

CROSS REFERENCES TO RELATED APPLICATIONS

The present application claims the benefit of U.S. Provisional Patent Application Ser. No. 60/696,001, filed Jul. 1, 2005 (Jul. 1, 2005).

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates generally to apparatus for monitoring patient movement, and more particularly to pressure pad for use on a chair, bed, or other surface typically occupied by a patient or resident and having an operably connected alarm system for alerting staff when the patient or resident has moved outside a defined area. Even more particularly, the present invention relates to a patient monitoring pressure pad having a time sensor and alarm that alerts hospital or residential care staff that the effective life of the pressure pad is nearing its end.

2. Discussion of Related Art including information disclosed under 37 CFR §§1.97, 1.98

Residential care facilities, particularly long-term residential care nursing facilities, must provide a considerable measure of protection to residents who may be impaired in their ability to care for themselves or to exercise sound judgment. Inherent in such care is the need to routinely confine residents to beds, chairs, showers, or other defined spaces or support apparatus, or alternatively to monitor patients and residents to ensure that the same do not wander into unsafe circumstances or outside the watchful care of the staff of the hospital or residential care facility. Accordingly, it is known to provide bed, chair, shower, and room occupancy monitoring systems to alert staff or attendants of inappropriate patient movement or mishaps.

For example, U.S. Pat. No. 5,410,297 to Joseph teaches a bed monitoring system including a capacitive sensor pad for placement under a patient. The pad comprises a foam plastic pad and heavy aluminum foil plates laminated on opposite sides of the foam. The plates are then adhesively bonded to the inner surfaces of an outer cover. The capacitor of the pad is connected in circuit with an oscillator and produces a frequency-related output. A ripple counter establishes a frequency-related output proportional to the capacitance. A microprocessor reads the counter output and samples are averaged to establish a reference base and the true weight affect of the patient on the sensing pad. Other factors which might effect the signal are readily attended to by programmed compensation. Each subsequent sample is averaged and compared with the reference base. If within a permitted range, the latest and current signal is averaged with the reference base and establishes a new base, and continuously tracks changes in the sensing system. A selected change in a selected time delay system actuates an alert or alarm system, which requires positive resetting to terminate the alarm system. The system is positively reset to return to normal position monitoring. The system may be set to automatically reset the alarm system after an alarm condition is established and then removed by the continuous tracking of the patient movement.

Also illustrative of the art, U.S. Pat. No. 5,654,694 to Newham U.S. Pat. No. 5,654,694 to Newham discloses a mobile patient monitoring system. The system includes a load sensor which detects the presence of a patient on a device and further includes a microprocessor responsive to a resident program. A first circuit connected to the microprocessor and to the sensor automatically activates operation of the microprocessor to a "monitor" mode upon detection by the sensor of the patient's presence on the device; it maintains operation of the microprocessor for a predetermined time period at least equal to a running time of the program; and it terminates operation of the microprocessor at the expiration of the predetermined time period after detection by the sensor of termination of the patient's presence on the device prior to expiration of the predetermined time period. A second circuit operates the system in response to commands manually applied to the second circuit to deactivate the system to a "hold/reset" mode after activating of the system to the "monitor" mode. The first circuit will also activate the system to the "monitor" mode after the system has been deactivated to the "hold/reset" mode together with subsequent detection by the sensor of termination of the patient's presence on the device and resumption of the patient's presence on the device. Alternatively, the microprocessor is responsive to the manually operable switch in the second circuit to activate the system to the "monitor" mode after the system has been deactivated to the "hold/reset" mode. A third circuit connected to the microprocessor provides an audio alarm upon demand by the microprocessor.

Patient monitoring pressure pads have a limited time during which their operation is entirely reliable. Accordingly, it is a common practice to have caregivers physical mark the pad with a date to ensure timely replacement before the operation either becomes unreliable or before total device failure. This system of monitoring the patient monitoring pad is unreliable and calls for specific staff action to remember to initiate, and then initiate, an affirmative act to prevent an important care facility device from becoming ineffective. There thus remains a need for a patient monitor pressure pad that provides care facility staff with an indication that the pad is nearing the end of its useful life. Preferably, the indication would be in the form of an audible alarm, such that care facility staff would be required to replace the pressure pad to eliminate an annoying alarm output.

The foregoing patents reflect the current state of the art of which the present inventor is aware. Reference to, and discussion of, these patents is intended to aid in discharging Applicant's acknowledged duty of candor in disclosing information that may be relevant to the examination of claims to the present invention. However, it is respectfully submitted that none of the above-indicated patents disclose, teach, suggest, show, or otherwise render obvious, either singly or when considered in combination, the invention described and claimed herein.

BRIEF SUMMARY OF THE INVENTION

The present invention is a patient monitor pressure pad for use in nursing homes, residential care facilities, hospitals, and other establishments that employ means to monitor the whereabouts of facility patients or residents. The pressure pad improves on prior art devices by providing a internal time sensor and alarm circuit that produces an audible or visible alarm output to alert facility care staff that the effective life of the pressure pad is nearing its end. It thus provides means to prevent use beyond the useful life of the pad and therefore to prevent needless accidents caused by unaccounted for patients or residents.

It is therefore an object of the present invention to provide a new and improved patient monitor pressure pad.

It is another object of the present invention to provide a new and improved patient monitor pressure pad that provides a conspicuous, perceptible signal that the useful life of the pressure pad is near its end.

A further object or feature of the present invention is a new and improved patient monitor pressure pad that alerts care givers with such a signal in either audible or visible form.

An even further object of the present invention is to provide a novel patient monitor pressure pad having various means for measuring and counting the useful life of the pressure pad before issuing an alarm signal.

Other novel features which are characteristic of the invention, as to organization and method of operation, together with further objects and advantages thereof will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty that characterize the invention are pointed out with particularity in the claims annexed to and forming part of this disclosure. The invention does not reside in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE SEVERAL VIEWS OF THE DRAWINGS

The invention will be better understood and the objects and advantages of the invention will become apparent when consideration is given to the following detailed description thereof. Such description makes reference to the annexed drawings wherein.

DETAILED DESCRIPTION OF THE INVENTION

Figure 1:
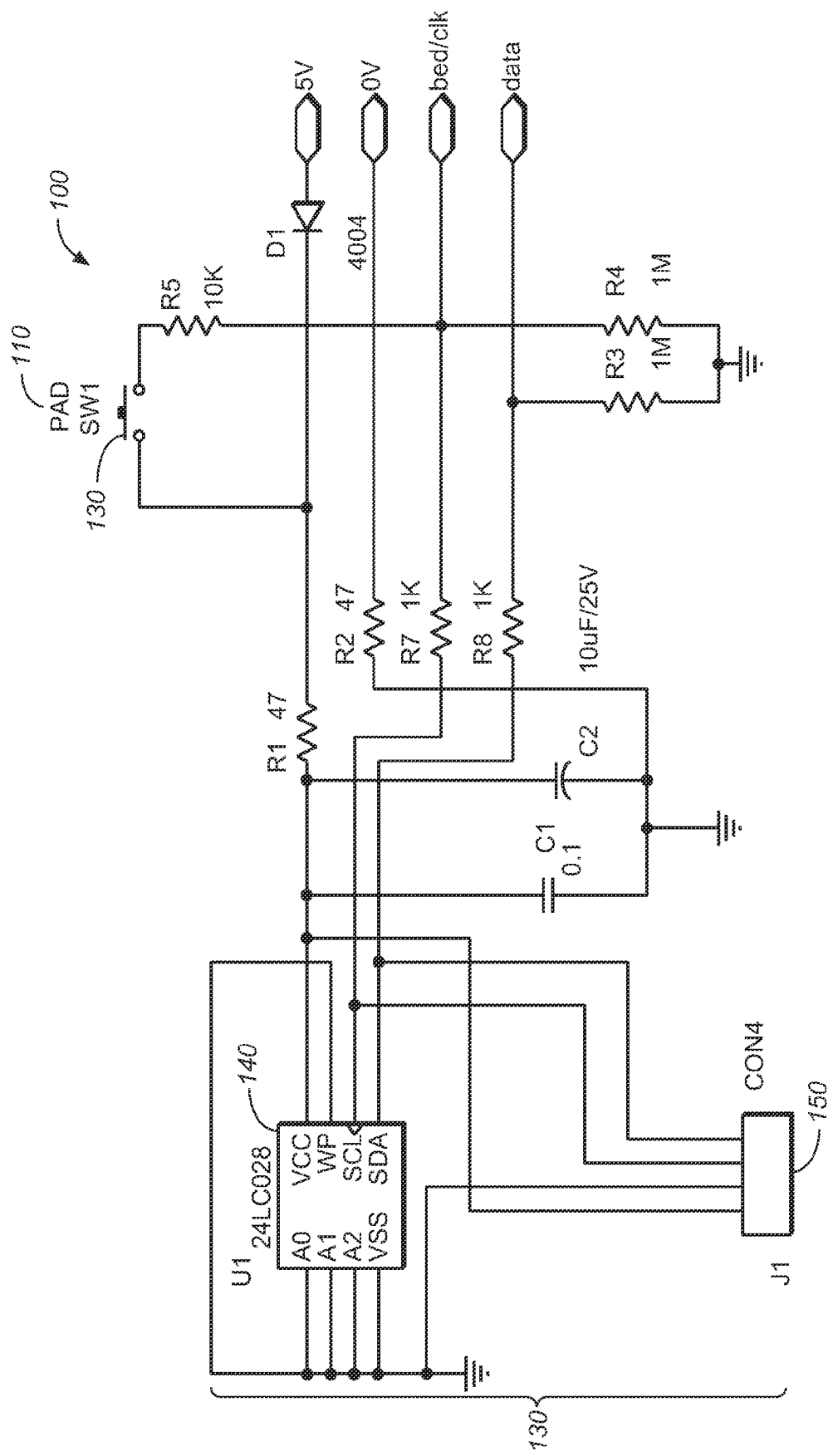
FIG. 1 is a circuit diagram showing a first preferred embodiment of a circuit for providing a "timed" patient monitor pad, viz, a patient monitor pressure pad having a timing circuit that sends a signal to induce an alarm output to alert persons that the useful and effective life of the pressure pad is nearing its end and should be replaced to ensure reliable performance.

Referring to FIGS. 1 through 6, there is illustrated a number of preferred embodiments of electrical circuits that may be employed to provide new and improved patient monitor pressure pad having a timing circuit to provide an effective date warning alert. The first preferred embodiment of the circuit enabling the alert is shown in FIG. 1 and is generally denominated 100 therein. This view shows a pressure pad 110 having an internal circuit 120 activated by a switch 130 when a patient sits, lies down on, or otherwise puts pressure on the pad. The circuit includes a memory chip, such as a Microchip Technology Inc. 24AA02/24LC02B 2 Kbit electrically erasable PROM 140, which is electrically and operatively connected to, and powered by, the pressure pad through a fixed multiple connector 150. The memory chip automatically updates only as the pad is used and the available useful and or effective life diminishes. This device counts down from a pre-selected number of hours of use (programmed into the EEPROM), and when the number of hours of acceptable use of the pad has been reached, the circuit emits a signal to elicit an alert output.

Figure 2:
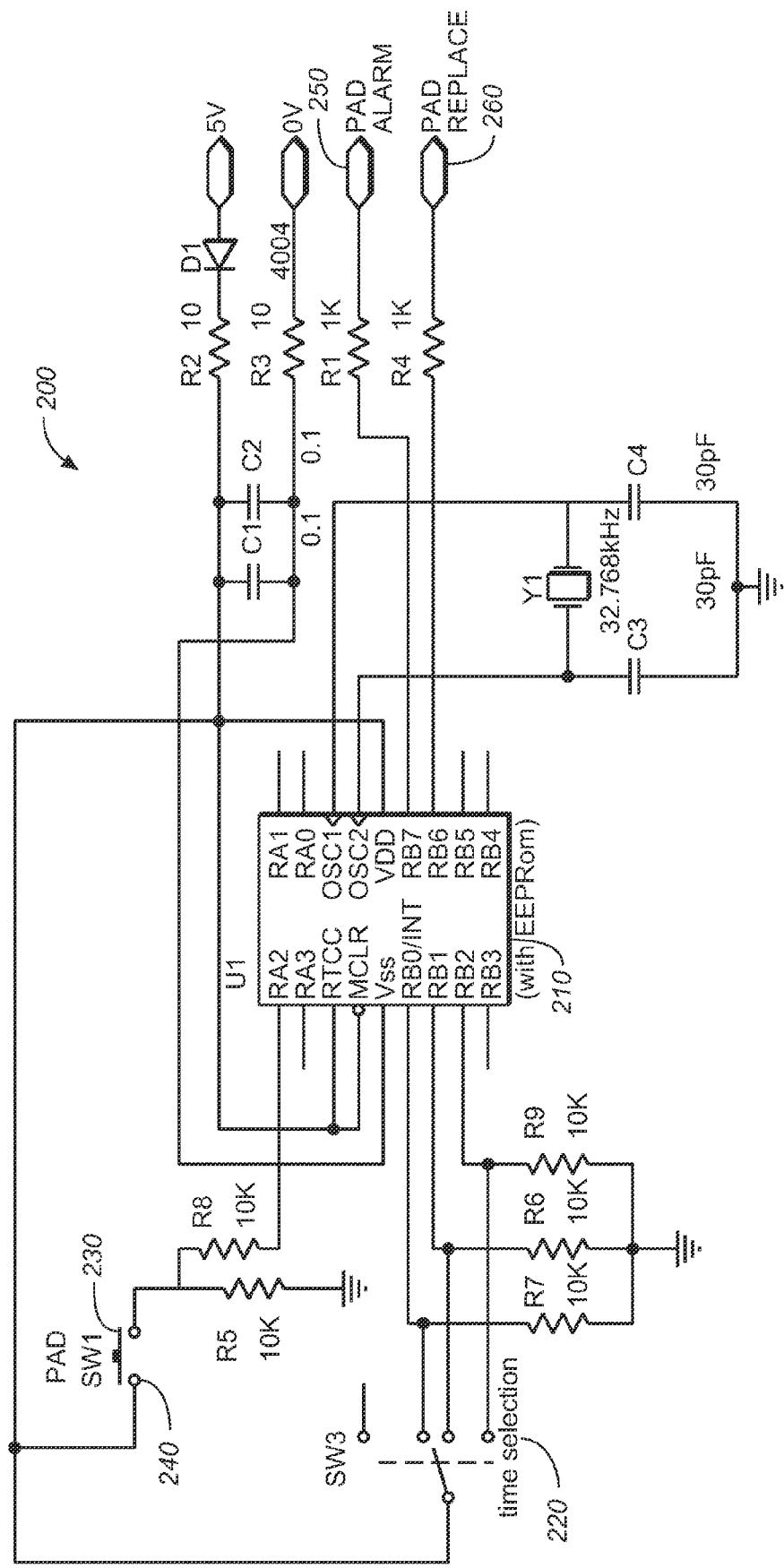
FIG. 2 is a second preferred embodiment of a circuit for the inventive apparatus.

FIG. 2 shows a second preferred embodiment 200 of a circuit employed in the present invention. In this embodiment, in addition to a microprocessor 210 (preferably with EEPROM) that performs the timing operation on a circuit and appropriately updates memory, the circuit also includes a time selection switch 220 (such as a ganged wafer switch) which allows the user to select among different periods of time that must elapse before an alarm is activated. Once again, when the pad 230 is used, switch 240 activates the circuit, and after the pre-determined time has passed, a perceptible alarm 250 is activated via the alarm circuit, which also issues a "pad replace" instruction output 260.

Figure 3:
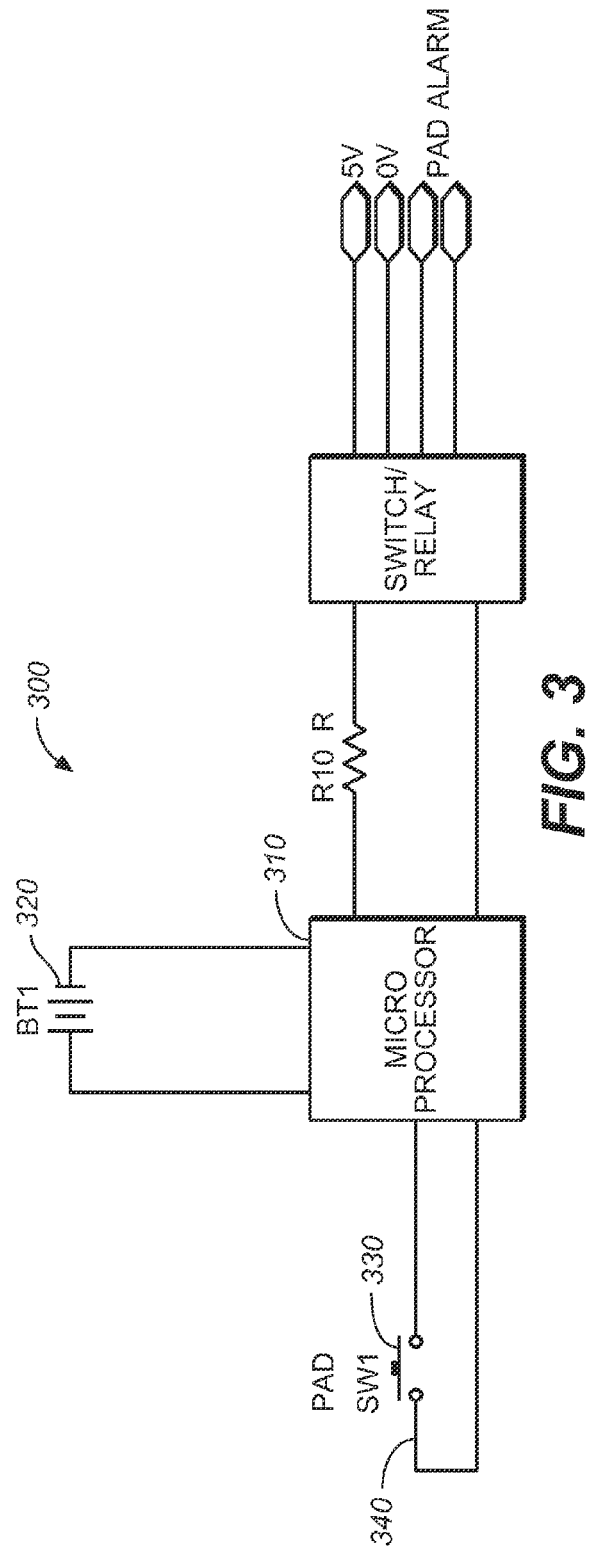
FIG. 3 is yet another, third embodiment, of the circuit for the inventive apparatus.

FIG. 3 shows a battery powered embodiment 300 of a circuit for the present invention, which also employs a microprocessor 310, but includes a battery 320 to power the circuit when electrical switch 330 is triggered by use of the pad 340. This circuit resembles the circuit shown in FIG. 2, but it can be employed as an aftermarket add-on to a pressure pad purchased separately in the market place. It will go into the alarm state when the predetermined time runs out.

Figure 4:
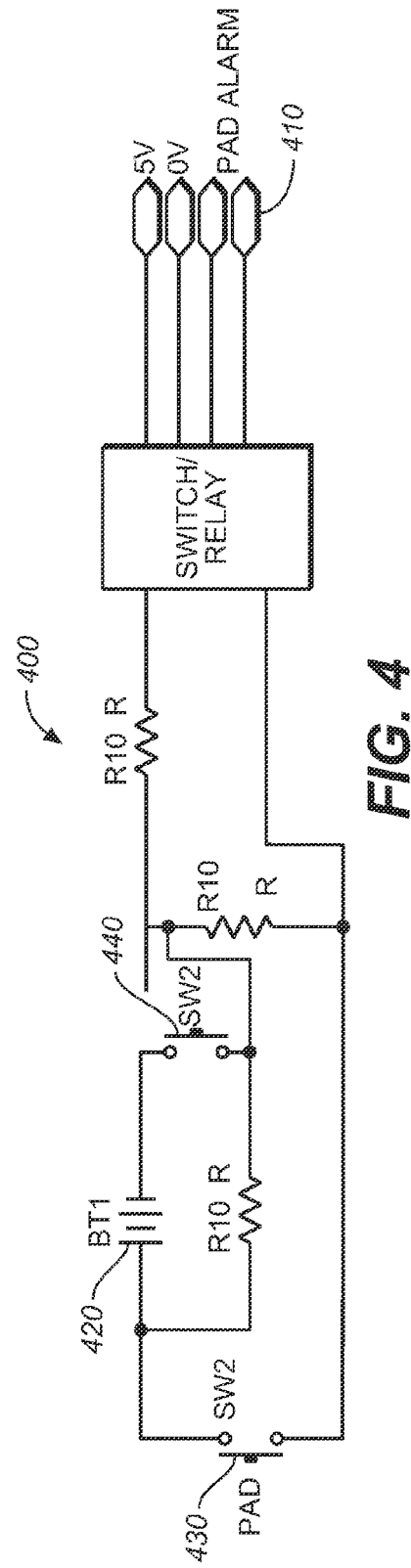
FIG. 4 is still another, fourth embodiment, of the circuit for the inventive apparatus.

FIG. 4 is yet another battery powered circuit 400 designed to emit an alarm 410 when the battery 420 runs low, rather than after use of the pad 430. The circuit must be manually turned on via the pad enable switch 440 to enable alarm operation and turn off with the same switch to conserve battery power.

Each of the circuits shown in FIGS. 3 and 4 will work with numerous patient pressure pad monitors and will go into the alarm condition only when a patient is lying on a bed. Those responsible for replacing worn units will be alerted to a pad that is approaching or has exceeded its useful operational life.

Figure 5:
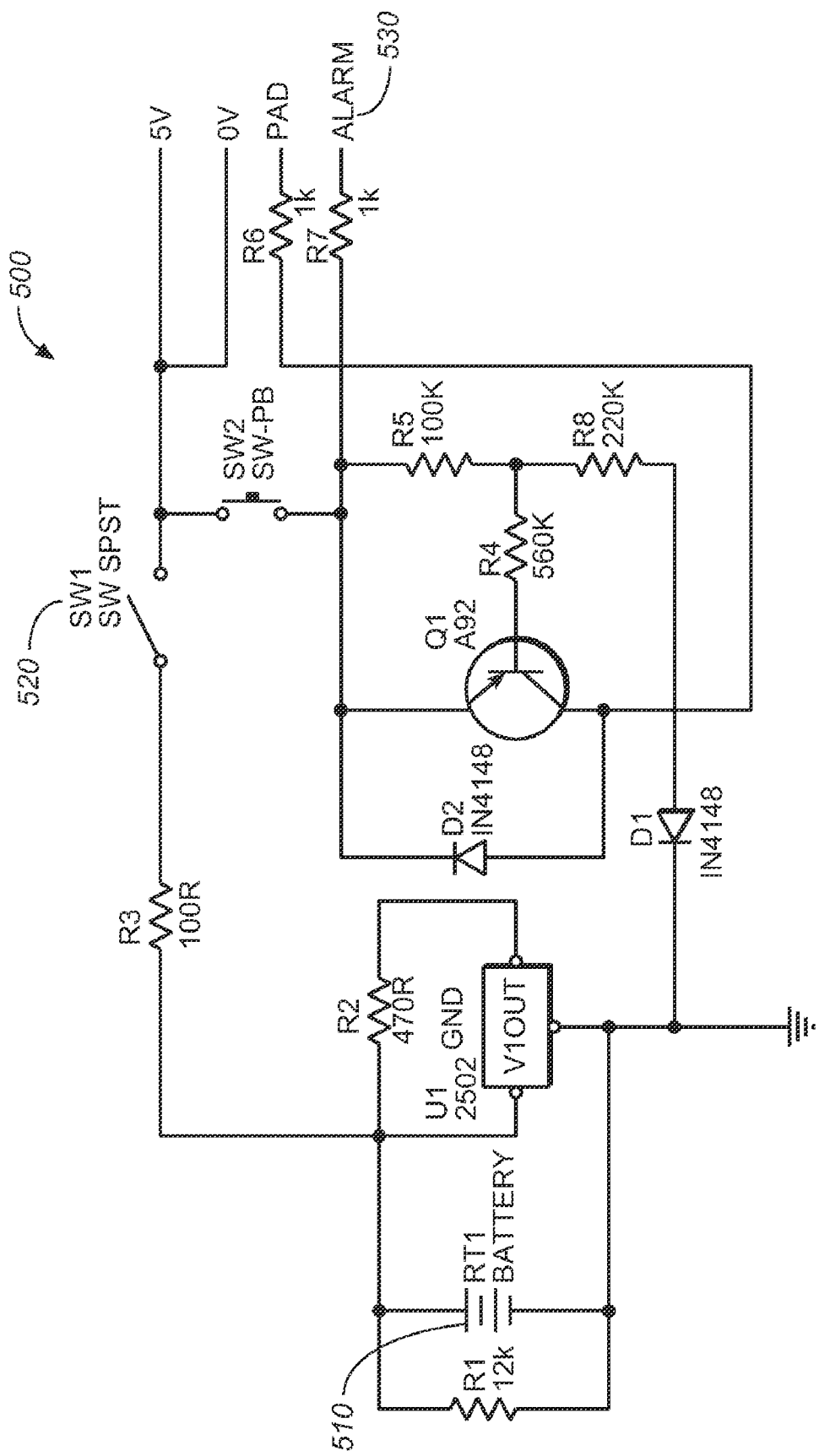
FIG. 5 shows a fifth preferred embodiment of a circuit for the inventive apparatus.

FIG. 5 shows a fifth preferred embodiment 500 of a circuit that may be used in the present invention. This circuit employs a battery 510 in conjunction with a dedicated "smart" monitor having a manually operable pad enable switch 520 and provides a dedicated "change pad" alert 530. Pads employing the circuits shown in each of FIGS. 4 and 5 must be switched off when not in use to conserve and extend battery life.

Figure 6:
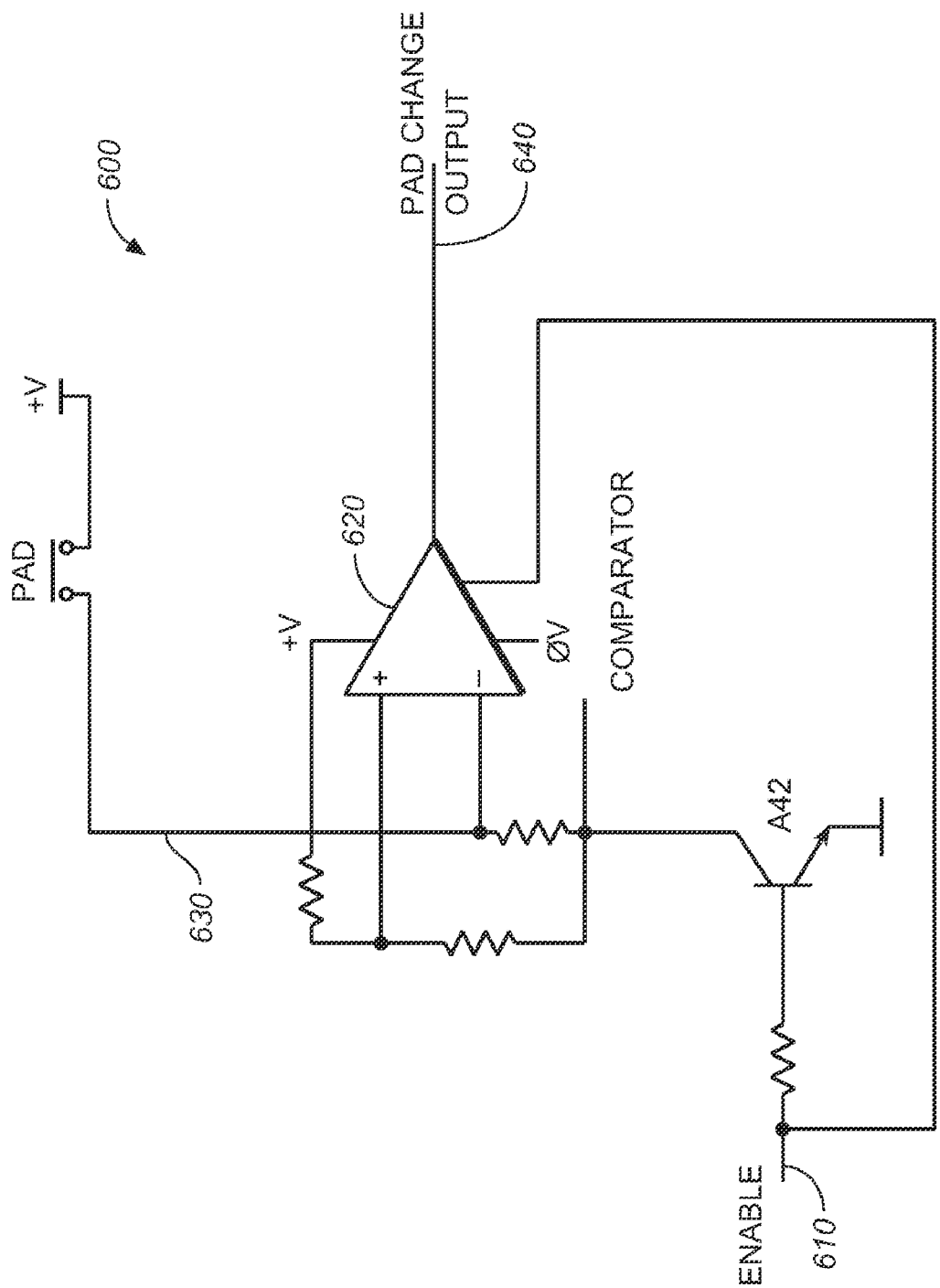
FIG. 6 shows a sixth and final preferred embodiment for the inventive "timed" patient monitoring pressure pad.

FIG. 6 is a schematic view showing a sixth preferred embodiment 600 of a circuit employed in the present invention. The foregoing circuits relied on the principle of timing pad use. The circuit of FIG. 6 is activated with a pad enable switch 610 and when on detects pad wear using a comparator 620, which measures increased resistance differential in the effective date alarm circuit on signal 630 resulting from component wear. When a threshold differential is reached, a "pad change" output signal 640 is emitted. This is a less reliable means of alerting caregivers to the need to replace a pad. However, it has the advantage of indicating such a need well in advance of a warranty period, particularly in the case of a faulty pad, poor performance, or excessive pad wear over a short period of time.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed is:

1. A patient monitor pressure pad, comprising:
    a pressure pad;
    a timing circuit operatively connected to said pressure pad, said timing circuit including a switch for activating said timing circuit when a patient puts pressure on said pressure pad, and a memory chip electrically and operatively connected to and powered by said pressure pad which updates only as the ad is used and the available effective life of said pressure pad diminishes, wherein said memory chip includes EEPROM and counts down from a pre-selected number of hours of use programmed into the EEPROM; and
    a perceptible alarm device electronically activate by said timing circuit for providing an effective date warning alert.

2. The apparatus of claim 1, wherein said timing circuit employs a comparator to measure increased resistance differential in said timing circuit.

3. The apparatus of claim 1, wherein said timing circuit is installed internally in said pressure pad.

4. The apparatus of claim 3, wherein said timing circuit includes a switch for activating said timing circuit when a patient puts pressure on said pressure pad, and a memory chip electrically and operatively connected to and powered by said pressure pad which updates only as the pad is used and the available effective life of said pressure pad diminishes.

5. The apparatus of claim 1, further including a time selection switch which allows the user to select among different periods of time that must elapse before an alarm is activated.

6. The apparatus of claim 5, wherein said alarm issues both a warning alert that the effective date of said pressure pad is nearing its end, and a pad replace instruction.

7. The apparatus of claim 1, wherein said timing circuit includes a battery power circuit and a battery.

8. The apparatus of claim 7, wherein said alarm device is activated to sound an alarm when said battery runs low.

9. The apparatus of claim 8, further including a manual pad enable switch to prevent inadvertent use and to conserve battery power.

* * * * *

UNITED STATES PATENT AND TRADEMARK OFFICE
CERTIFICATE OF CORRECTION

PATENT NO.         : 7,557,719 B1
APPLICATION NO. : 11/480784
DATED              : July 7, 2009
INVENTOR(S)        : Timothy Long and Steven Alfred Williams It is certified that error appears in the above-identified patent and that said Letters Patent is hereby corrected as shown below:

On the Title Page Item (75) should read,

TIMOTHY LONG and STEVEN ALFRED WILLIAMS

Signed and Sealed this

Tenth Day of November, 2009

David J. Kappos
*Director of the United States Patent and Trademark Office*